United States Patent [19]

Dutta et al.

[11] 4,124,703
[45] Nov. 7, 1978

[54] LULIBERIN ANALOGS

[75] Inventors: Anand S. Dutta; Michael B. Giles, both of Macclesfield, England

[73] Assignee: Imperial Chemical Industries Limited, London, England

[21] Appl. No.: 800,853

[22] Filed: May 26, 1977

[30] Foreign Application Priority Data

Oct. 12, 1976 [GB] United Kingdom ............... 42318/76

[51] Int. Cl.$^2$ ..................... A61K 37/00; C07C 103/52
[52] U.S. Cl. ............................ 424/177; 260/112.5 LH
[58] Field of Search ............... 260/112.5 LH; 424/177

[56] References Cited

U.S. PATENT DOCUMENTS 3,928,307  12/1975  Foell et al. .................. 260/112.5 LH

OTHER PUBLICATIONS

A. S. Dutta, et al., Clinical Endocrinology (1976) pp. 291S-298S.

*Primary Examiner*—Delbert R. Phillips
*Attorney, Agent, or Firm*—Cushman, Darby & Cushman

[57] ABSTRACT

The disclosure relates to novel polypeptides which are analogues of luliberin and which possess luliberin antagonist activity, to processes for their manufacture and to compositions containing them. Typical of the polypeptides disclosed is

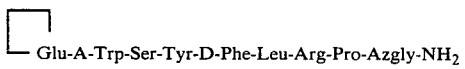
Glu-A-Trp-Ser-Tyr-D-Phe-Leu-Arg-Pro-Azgly-NH$_2$ in which A is D-Phe, D-Trp or a direct bond.

3 Claims, No Drawings

LULIBERIN ANALOGS

This invention relates to a polypeptide, its manufacture and pharmaceutical and veterinary compositions containing it, and in particular it relates to a polypeptide which inhibits the ovulatory action of luliberin, luliberin being the internationally-approved name for LH—RF (luteinising hormone releasing factor) (*J.Biol.-Chem.*, 1975, 250, 3215).

It is known (D. H. Coy, F. Labrie, M. Savary, E. J. Coy and A. V. Schally, *Molecular and Cellular Endocrinology*, 1976, 5, 201–208) that substitution of D-phenylalanine for the histidine and glycine residues at positions 2 and 6 respectively of the luliberin molecule produces a compound [D-Phe², D-Phe⁶] luliberin, which has luliberin antagonist properties. In has now been found that the additional substitution of azaglycine for the glycine at position 10 of such an analogue produces a compound which is surprisingly much more potent as an antagonist of the effects of luliberin.

According to the invention there is provided a polypeptide of the formula:

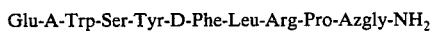 I
Glu-A-Trp-Ser-Tyr-D-Phe-Leu-Arg-Pro-Azgly-NH₂ in which A stands for the D-Phe or D-Trp residue or for a direct bond, and the pharmaceutically- or veterinarily-acceptable acid-addition salts thereof.

In the above formula I and throughout this specification, the amino-acid residues are designated by their standard abbreviations (*Pure and Applied Chemistry*, 1974, 40, 317). Where the configuration of a particular amino-acid is not designated, that amino-acid, apart from Azgly, has the natural L-configuration. Azgly is the abbreviation used to describe the compound azaglycine, of the formula H₂N.NH.COOH, which can be regarded as an analogue of glycine H₂N.CH₂.COOH, in which the methylene group has been replaced by an NH group. The compound named azaglycine amide is thus also known as semicarbazide, H₂N.NH.CONH₂.

Particular compounds of the invention are as follows:
That wherein A is D-Phe.
That wherein A is D-Trp.
That wherein A is a direct bond.

The preferred compound of the invention is that wherein A is D-Phe.

A particular pharmaceutically- or veterinarily-acceptable acid-addition salt is, for example, a hydrochloride, phosphate, citrate or acetate.

The polypeptide of the invention may be manufactured by methods known in themselves for the manufacture of chemically-analogous compounds. Thus the following processes, A having the meaning stated above, are provided as further features of the invention:

(a) removal of one or more conventional peptide protecting groups from a protected polypeptide to give the compound of the formula I;

(b) reaction of

  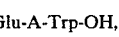
Glu-OH, Glu-A-OH, Glu-A-Trp-OH,

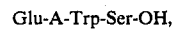
Glu-A-Trp-Ser-OH,

Glu-A-Trp-Ser-Tyr-OH,

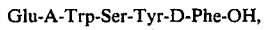
Glu-A-Trp-Ser-Tyr-D-Phe-OH,

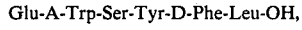
Glu-A-Trp-Ser-Tyr-D-Phe-Leu-OH,

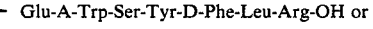
Glu-A-Trp-Ser-Tyr-D-Phe-Leu-Arg-OH or

Glu-A-Trp-Ser-Tyr-D-Phe-Leu-Arg-Pro-OH, or a suitable activated derivative of any of these, with H-A-Trp-Ser-Tyr-D-Phe-Leu-Arg-Pro-Azgly-NH₂, H-Trp-Ser-Tyr-D-Phe-Leu-Arg-Pro-Azgly-NH₂, H-Ser-Tyr-D-Phe-Leu-Arg-Pro-Azgly-NH₂, H-Tyr-D-Phe-Leu-Arg-Pro-Azgly-NH₂, H-D-Phe-Leu-Arg-Pro-Azgly-NH₂, H-Leu-Arg-Pro-Azgly-NH₂, H-Arg-Pro-Azgly-NH₂, H-Pro-Azgly-NH₂ or H-Azgly-NH₂ respectively, or a suitable activated derivative or any of these, in a standard peptide coupling reaction; or (c) reaction of a suitable derivative of a carboxylic acid of the formula:

 II
Glu-A-Trp-Ser-Tyr-D-Phe-Leu-Arg-Pro-Azgly-OH with ammonia.

In process (a) there may be as many protecting groups in the starting material as there are radicals which may require protection, for example some or all of those radicals which exist in the product as free OH radicals or basic NH radicals.

In process (a) the protecting group or groups may be those described in a standard text book on peptide chemistry, for example M. Bodansky and M. A. Ondetti, "Piptide Synthesis", Interscience, New York, 1966, Chapter IV; F. M. Finn and K. Hofmann, "The Proteins", Vol.II, edited by H. Neurath and R. L. Hill, Academic Press Inc., New York, 1976, p.106; "Aminoacids, Peptides and Proteins" (Specialist Periodical Reports), The Chemical Society, London, volumes 1 to 8. Various methods for the removal of the protecting groups are also described in these books.

In process (a) a particularly useful NH protecting group is the benzyloxycarbonyl radical and a particularly useful OH protecting group is the benzyl radical. Both these groups may be readily removed by hydrogenolysis, for example in the presence of a palladium-on-charcoal catalyst.

In process (a) a further particularly useful NH protecting group is the t-butoxycarbonyl radical and a further particularly useful OH protecting group is the t-butyl radical. Both these groups may be readily removed by treatment with an acid such as hydrogen chloride or trifluoroacetic acid.

In process (a) a further particularly useful NH protecting group is the benzyloxycarbonyl or t-butoxycarbonyl radical and a particularly useful OH protecting group is the t-butyl radical. These protecting groups may be readily removed by treatment with HBr in acetic acid.

The deprotection process (a) can also involve removal from a resin used in solid phase synthesis according to Merrifield (R. B. Merrifield, *Advances in Enzymology*, 1969, 32, 221).

In process (b) any one of the standard peptide coupling reactions may be used, for example those described in a standard text book on peptide chemistry, for example the above text book by Bodansky and Ondetti, Chapter V, and the above volumes 1 to 8 of Specialist Periodical Reports of the Chemical Society.

In process (b) a particular coupling reaction is an azide coupling, an active ester coupling or a coupling involving N,N'-dicyclohexylcarbodi-imide and 1-hydroxybenzotriazole. A preferred coupling reaction is an azide coupling, and in particular such a coupling which forms the Ser-Tyr peptide bond.

In process (c) a suitable activated derivative of the starting material is, for example, an ester. In the case of an activated derivative the reaction may be conducted by bringing the activated derivative into contact with ammonia in the presence of a diluent or solvent.

The starting materials for use in the processes of the invention may be prepared from known compounds by standard peptide coupling reactions, standard peptide protection reactions and standard peptide deprotection reactions well known to one skilled in this art, for example as set out in Examples 1 to 3.

As noted above, the polypeptide of the invention has luliberin antagonist properties, that is it inhibits the actions of luliberin, a natural hormone secreted by the hypothalamus which acts on the pituitary gland causing it to release luteinsisting hormone (LH) and follicle stimulating hormone (FSH). These two pituitary hormones are involved in controlling reproductive processes, the latter, FSH, acting on the ovaries to promote maturation of follicles and the former, LH, to induce ovulation. This inhibitory property can be demonostrated by the effect of the polypeptide of the invention in preventing ovulation in androgen-sterilised constant-oestrus rats when injected simultaneously with luliberin (0.5 μg./rat), or by its ability, when dosed simultaneously with luliberin, to inhibit the release of LH and FSH, as measured by double antibody radioimmunoassay, into the blood plasma of immature male rats. The polypeptide of the invention may therefore be used for fertility control.

The above test on androgen-sterilised rats is carried out as follows:

Androgen-sterilised female rats prepared by treating rats at days 3, 4 and 5 of age with 100 μg. testosterone propionate have a persistent oestrus vaginal smear and numerous preovulatory follicles in the ovaries. Administration of luliberin causes the release of an ovulatory surge of LH and FSH which can be assessed by the presence of ova in the Fallopian tubes and fresh corpora lutea in the ovaries. This effect of luliberin is completely blocked when a polypeptide of formula I is administered along with it.

All the compounds exemplified in this specification show no overt toxic effects when dosed at at least four times their minimum active dose. In particular the preferred compound of the invention, that described in Example 1, displays no overt toxic effects when dosed at 20 times its minimum effective dose.

According to a further feature of the invention there is provided a pharmaceutical or veterinary composition which comprises as active ingredient the polypeptide of the invention in association with a pharmaceutically- or veterinarily-acceptable diluent or carrier.

The composition of the invention may, for example, be in a form suitable for oral or buccal administration, for example a tablet, capsule, solution or suspension; nasal administration, for example a snuff, nasal spray or nasal drops; vaginal or rectal administration, for example a suppository; or parenteral administration, for example a sterile injectable solution or suspension.

In general, the above compositions may be prepared in a conventional manner using conventional excipients. However, in the case of a composition for oral administration, it may be convenient for the composition to include a coating to protect the polypeptide active ingredient from the actions of enzymes in the stomach.

A preferred composition of the invention is one suitable for oral administration in unit dosage form, for example a tablet, capsule, drench or bolus which contains from 25 mg. to 5 g., and preferably 100 mg. to 1 g., of polypeptide in each unit dose, or one suitable for parenteral administration which contains from 50 μg. to 10 mg. of polypeptide per ml., and preferably 100 μg. to 1 mg. of polypeptide per ml. of solution.

A parenteral composition is preferably a solution in isotonic saline or isotonic dextrose, buffered if necessary to a pH of 5 to 9, or a solution or suspension in oil, for example corn oil or polyethoxylated castor oil. Alternatively, the parenteral composition may be one designed for slow release in which case the amount of polypeptide per unit dose is in general greater than that required when a conventional injectable formulation is used. A preferred slow release parenteral formulation contains from 1 μg. to 10 mg. of polypeptide per unit dose.

The composition of the invention will normally be administered such that a daily oral dose will be from 500 μg./kg. to 200 mg./kg., and a daily parenteral dose, for example by intravenous, subcutaneous or intramuscular injection or infusion, will be from 2 μg./kg. to 1 mg./kg. In humans these doses are equivalent to a total daily dose of 35 mg. to 14 g. administered orally and a total daily dose of 140 μg. to 70 mg. administered parenterally. When administered via the mucous membranes, the dose ranges will be intermediate between the oral and parenteral ranges given above.

The invention is illustrated, but not limited, by the following Examples:

In the Examples, $R_f$ refers to ascending thin layer chromatography (t.l.c.) on silica gel plates (Kieselgel G). The solvent systems used in this chromatography were butan-1-ol/acetic acid/water (4:1:5 v/v) ($R_fA$), butan-1-ol/acetic acid/water/pyridine (15:3:12:10 v/v) ($R_fB$), butan-2-ol/3% w/v aqueous ammonium hydroxide (3:1 v/v) ($R_fC$), acetonitrile/water (3:1 v/v) ($R_fD$), acetone/chloroform (1:1 v/v) ($R_fE$), chloroform/ethanol (1:4 v/v) ($R_fF$), cyclohexane/ethyl acetate (1:1 v/v) ($R_fG$), cyclohexane/ethyl acetate/methanol (1:1:1 v/v) ($R_fH$), chloroform/methanol/water (11:8:2 v/v) ($R_fK$), chloroform/methanol (19:1 v/v) ($R_fP$) and chloroform/methanol (9:1 v/v) ($R_fQ$). In all cases, plates were examined under U.V. light and treated with fluorescamine, ninhydrin, and chlorine-starch-iodide reagents. Unless otherwise stated, the quoting of an $R_f$ implies that a single spot revealed by these methods.

Acid hydrolysates of all products described in this specification were prepared by heating the peptide or protected peptide with 6N-hydrochloric acid containing 1% w/v phenol in a sealed evacuated tube for 16 hours at 100° C. The amino-acid composition of each hydrolysate was determined with a LoCarte Amino-acid Analyser, and in each case was in agreement with the expected composition. The term "worked up in the usual manner" used in the Examples implies that after the reaction any solid residue was removed by filtration, the filtrate evaporated to dryness below 40° C., the residue in ethyl acetate was washed with a 20% citric acid solution, water, saturated sodium hydrogen carbonate solution and water, dried over anhydrous sodium sulphate and the ethyl acetate was evaporated in vacuo to leave the compound.

In the Examples the following contractions are used:
OCP — 2,4,5-trichlorophenyl ester
Bzl — benzyl
Z — benzyloxycarbonyl
BOC — t-butoxycarbonyl
'Sephadex' is a Trade Mark.

EXAMPLE 1

Synthesis of
L-pyroglutamyl-D-phenylalanyl-L-tryptophyl-L-seryl-L-tyrosyl-D-phenylalanyl-L-leucyl-L-arginyl-L-prolylazaglycine amide To a cooled (0° C.) and stirred suspension of L-pyroglutamyl-D-phenylalanyl-L-tryptophyl-L-serine hydrazide (0.275 mmole) in dimethylformamide (1.0 ml.) was added 5.92M hydrogen chloride in dioxan (1.1 mmole). The clear solution obtained after several minutes stirring was further cooled to −20° C. and to it was added t-butyl nitrite (0.29 mmole). Stirring was continued for 20 minutes at −20° C. and the solution was neutralised by the addition of triethylamine (1.1 mmole). A precooled −20° C. mixture of L-tyrosyl-D-phenylalanyl-L-leucyl-L-arginyl-L-prolylazaglycine amide dihydrochloride (0.25 mmole, obtained by the hydrogenolysis of N-benzyloxycarbonyl-O-benzyl-L-tyrosyl-D-phenylalanyl-L-leucyl-($N^\omega$-nitro)-L-arginyl-L-prolylazaglycine amide in 80% v/v aqueous methanol for 40 hours over 5% w/w palladium-on-charcoal in the presence of 2 equivalents of hydrogen chloride) and triethylamine (0.25 mmole) in dimethylformamide (1.0 ml.) was added. The mixture was stirred for 24 hours at 4° C. The reaction mixture was applied directly to a 'Sephadex' LH-20 column using dimethylformamide as eluant. The peptide was further purified by partition chromatography on 'Sephadex' G-25 using the solvent system, n-butanol-acetic acid-water-pyridine (5:1:5:1 v/v), yield 59.2%, $R_fA$ 0.55, paper electrophoresis at pH 2.1 showed a single spot, $R_f$ (relative to luliberin) 0.46.

The starting materials for use in the above procedure may be obtained as set out in the following scheme 1.

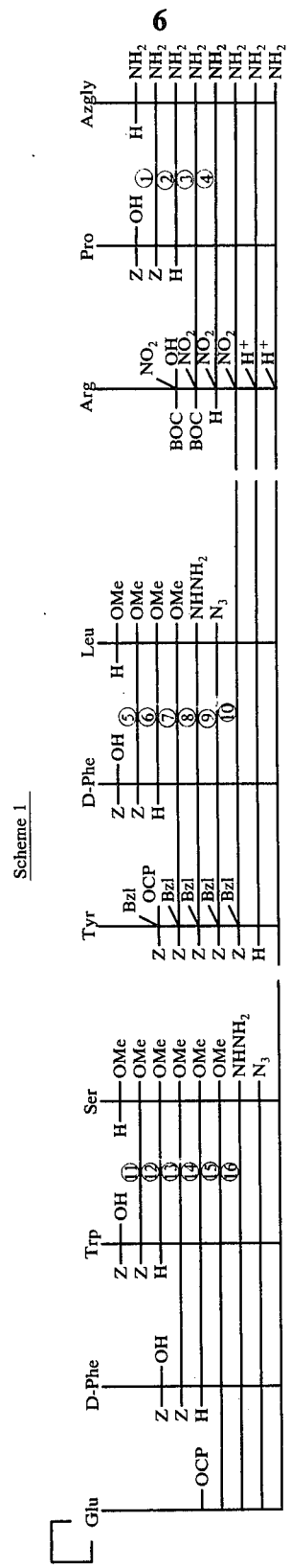

Scheme 1

Step ①

To a stirred and cooled (0° C.) suspension of N-benzyloxycarbonyl-L-proline (24.9 g., 100 m mole), semicarbazide hydrochloride (11.2 g., 100 m mole) and triethylamine (14.5 ml., 100 m mole) in dimethylformamide (200 ml.), dicyclohexylcarbodiimide (20.6 g., 100 m mole) was added and stirring was continued for 16 hours at 4° C. Dicyclohexylurea was removed by filtration and the filtrate was evaporated to a small volume. Water (200 ml.) was added and the solution was extracted with ethyl acetate (3 × 50 ml.). The product precipitated out of the aqueous solution in about an hour. Recrystallisation from aqueous methanol gave the dipeptide amide (16.5 g., 53.9%), m.p. 189°–190° C., $[\alpha]_D^{24} -43.6°$ (c, 1.4 in dimethylformamide), $R_fD$ 0.54, $R_fF$ 0.52, $R_fH$ 0.38, $R_fK$ 0.78.

Step ②

Catalytic reduction over 5% w/w palladium-on-charcoal in 80% v/v aqueous dimethylformamide for 6 hours at room temperature in presence of two equivalents of hydrogen chloride.

Step ③

A solution of $N^\alpha$-t-butoxycarbonyl-$N^\omega$-nitro-L-arginine (13.5 g., 42.3 m mole), L-prolylazaglycine amide hydrochloride (9.81 g., 47 m mole), 1-hydroxybenzotriazole (11.5 g., 82 m mole) and triethylamine (6.58 ml., 47 m mole) was cooled to 0° C. and dicyclohexylcarbodi-imide (9.13 g., 44.4 m mole) was added. The reaction mixture was stirred overnight at 4° C., filtered to remove the solid material, and the filtrate was evaporated to dryness in vacuo. The residue was partitioned between ethyl acetate and water by counter current distribution (4 transfers). The aqueous phases were combined, evaporated to dryness, and the residue was partitioned between n-butanol and 5% w/v aqueous acetic acid by counter current distribution (12 transfers). The crude peptide obtained by evaporating the combined n-butanol phases was purified by silica gel column chromatography using 5% v/v methanol in chloroform, 10% v/v methanol in chloroform and 20% v/v methanol in chloroform as eluting solvents. The product containing fractions were combined, evaporated to dryness, and an aqueous solution of the residue was passed through an anion exchange resin (AG-1×-2) column to remove $N^\alpha$-t-butoxycarbonyl-$N^\omega$-nitro-arginine. The column was then washed with water, and the combined aqueous phases and the washings were freeze dried, to give the azapeptide derivative, yield 13.82 g. (69%), m.p. 135°–136° C., $R_fA$ 0.49, $R_fB$ 0.65, $R_fC$ 0.46, $R_fD$ 0.64, $R_fF$ 0.35, $R_fH$ 0.19, $R_fK$ 0.86.

Step ④

N-t-Butoxycarbonyl derivative was dissolved in ethyl acetate and treated with 3NHCl in ethyl acetate solution (4 equivalents) for 1 hour at room temperature.

Step ⑤

A solution of N-benzyloxycarbonyl-D-phenylalanine (7.41 g., 24.8 m moles) and L-leucine methyl ester (3.62 g., 25 m moles) in ethyl acetate (100 ml.) was cooled to 0° C. and dicyclohexylcarbodi-imide (5.15 g., 25 m mole) was added to it. The reaction mixture was stirred overnight at 4° C. The usual work up followed by recrystallisation of the residue from ethyl acetate/petroleum ether (b.p. 60°–80° C.) gave the dipeptide (9.1 g., 86%), m.p. 123°–124° C., $[\alpha]_D^{26} -18.7°$ (c, 2.1 in methanol), $R_fD$ 0.76, $R_fE$ 0.65, $R_fF$ 0.74, $R_fH$ 0.73.

Step ⑥

Catalytic reduction over 5% w/w palladium-on-charcoal in ethanol containing one equivalent of hydrogen chloride for 5 hours.

Step ⑦

To a stirred solution of N-benzyloxycarbonyl-O-benzyl-L-tyrosine 2,4,5-trichlorophenyl ester (4.89 g., 8.36 m mole) and D-phenylalanyl-L-leucine methyl ester hydrochloride (2.5 g., 7.6 m mole) in dimethylformamide, triethylamine (1.1 ml., 7.6 m mole) was added and the stirring was continued overnight at room temperature. Triethylamine hydrochloride was filtered off and the filtrate was evaporated to dryness. Recrystallisation of the residue from aqueous methanol gave the tripeptide derivative, 3.6 g., (69.7%), m.p. 183°–184° C., $R_fD$ 0.82, $R_fE$ 0.69, $R_fH$ 0.78, $R_fP$ 0.71, $R_fQ$ 0.82.

Step ⑧

A solution of the preceeding methyl ester (3.42 g., 5.04 m mole) and hydrazine hydrate (60 m mole) in dimethylformamide (30 ml.) was stirred at room temperature for 4 hours, concentrated to a small volume and the hydrazide was precipitated by the addition of water (500 ml.). It was collected, washed with water, methanol/ether (1:4 v/v) and ether and dried. Yield 2.94 g. (85.9%), m.p. 179°–180° C., $R_fA$ 0.81, $R_fB$ 0.79, $R_fC$ 0.88, $R_fD$ 0.69, $R_fE$ 0.49, $R_fF$ 0.65, $R_fH$ 0.67, $R_fP$ 0.25, $R_fQ$ 0.57.

Steps ⑨ and ⑩

A solution of 6.02 M hydrogen chloride in dioxan (1.83 ml., 11 m mole) was added to a solution of N-benzyloxycarbonyl-O-benzyl-L-tyrosyl-D-phenylalanyl-L-leucine hydrazide (1.86 g., 2.75 m mole) in dimethylformamide (5 ml.) at −20° C. followed by t-butyl nitrite (0.33 ml., 2.89 m mole). After 2 minutes a precooled (−20° C.) solution of triethylamine (1.89 ml., 13.5 m mole) and $N^\omega$-nitro-L-arginyl-L-prolylazaglycine amide hydrochloride (1.02 g., 2.5 m mole) in dimethylformamide (10 ml.) was added and the reaction mixture was stirred overnight at 4° C. Usual work up gave the hexapeptide derivative which was further purified by silica gel (120 g.) column chromatography using 5% v/v methanol in chloroform, 10% v/v methanol in chloroform and a mixture of chloroform/methanol/water (11:8:2 v/v) as eluting solvents, yield 0.74 g. (29.3%), m.p. 137°–139° C., $R_fA$ 0.68, $R_fB$ 0.72, $R_fC$ 0.58, $R_fD$ 0.62, $R_fH$ 0.39, $R_fK$ 0.95.

Step ⑪

To a vigorously stirred and cooled (−20° C.) solution of N-benzyloxycarbonyl-L-tryptophane (33.84 g., 100 mmole) and N-methyl morpholine (11.0 ml., 100 mmole) in tetrahydrofuran (200 ml.), ethyl chloroformate (9.0 ml., 95 mmole) was added. After 2 min. a precooled (−20° C.) solution of L-serine methyl ester hydrochloride (17.10 g., 110 mmole) and N-methyl morpholine (12.1 ml., 110 mmole) in dimethylformamide (150 ml.) was added and the stirring was continued at −20° C. for 30 min. and at room temperature for 3 hours. Usual work up gave an oil. Two crystallisations from ethyl acetate/petroleum ether (b.p. 60°–80° C.) gave the dipeptide derivative (30.53 g., 69.5%), m.p.

140.5°–141° C., [α]$_D^{24}$ −22.13° (c, 1.4 in dimethylformamide).

Step ⑫

Catalytic reduction in 80% v/v aqueous dimethylformamide over 5% w/w palladium-on-charcoal for 5 hours.

Step ⑬

A solution of N-benzyloxycarbonyl-D-phenylalanine (2.99 g., 10 mmole), L-tryptophyl-L-serine methyl ester hydrochloride (3.41 g., 10 mmole), 1-hydroxybenzotriazole (2.70 g., 20 mmole) and triethylamine (1.40 ml., 11 mmole) in dimethylformamide was cooled to 0° C. and dicyclohexylcarbodiimide (2.27 g., 11 mmole) was added to it. The reaction mixture was stirred at room temperature for 72 hours and was worked up in the usual manner. The residue was recrystallised from hot ethyl acetate. Yield 4.89 g. (83.4%), m.p. 195°–197° C., R$_f$A 0.86, R$_f$B 0.81, R$_f$C 0.85, R$_f$D 0.72, R$_f$E 0.37, R$_f$F 0.63, R$_f$H 0.67, R$_f$P 0.15, R$_f$Q 0.53.

Step ⑭

Catalytic reduction with 5% w/w palladium-on-charcoal in a mixture of ethanol-dimethylformamide (1:1 v/v) for 5 hours at room temperature in the presence of 1.1 equivalent of hydrogen chloride.

Step ⑮

A solution of L-pyroglutamic acid 2,4,5-trichlorophenyl ester (2.62 g., 8.5 m mole), D-phenylalanyl-L-tryptophyl-L-serine methyl ester hydrochloride (3.75 g., 7.7 m mole), and triethylamine (1.08 ml., 7.7 m mole) in dimethylformamide (30 ml.) was stirred overnight at room temperature and then concentrated to dryness in vacuo. The residue was triturated with ethyl acetate and water and filtered off, washed with methanol-ether (1:5 v/v), and ether and dried. The crude peptide was crystallised from methanol-ether to yield the tetrapeptide derivative (2.15 g., 49.3%), m.p. 194°–196° C., R$_f$A 0.68, R$_f$B 0.76, R$_f$C 0.70, R$_f$D 0.66, R$_f$H 0.38, R$_f$Q 0.18.

Step ⑯

A solution of L-pyroglutamyl-D-phenylalanyl-L-tryptophyl-L-serine methyl ester (2.03 g., 3.6 m mole) in dimethylformamide (20 ml.) was treated with hydrazine hydrate (72 m mole). After 6 hours, the solvent was removed by evaporation in vacuo and the residue was triturated with water, filtered off, washed with water, methanol-ether (1:5 v/v), ether and dried to yield the tetrapeptide hydrazide (1.73 g., 84.7%), m.p. 234° C. (decomp.), R$_f$A 0.58, R$_f$B 0.81, R$_f$C 0.58, R$_f$D 0.66, R$_f$K 0.70.

EXAMPLE 2

Synthesis of L-pyroglutamyl-D-tryptophyl-L-tryptophyl-L-seryl-L-tyrosyl-D-phenylalanyl-L-leucyl-L-arginyl-L-prolylazaglycine amide t-Butyl nitrite (30 μl., 0.25 mmole) was added to a cooled (−20° C.) and stirred solution of L-pyroglutamyl-D-tryptophyl-L-tryptophyl-L-serine hydrazide (151 mg., 0.25 mmole) and 5.9M HCl in dioxane (170 μl., 1 mmole) in dimethylformamide (2 ml.). Triethylamine (142 μl., 1 mmole) was added after 20 minutes, followed by a precooled (−20° C.) solution of L-tyrosyl-D-phenylalanyl-L-leucyl-L-arginyl-L-prolylazaglycine amide dihydrochloride (197 mg., 0.25 mmole, prepared as in Example 1), and triethylamine (36 μl., 0.25 mmole) in dimethylformamide (2 ml.). The reaction mixture was stirred overnight at 4° C. It was then applied to 'Sephadex' LH-20 column which was then eluted with dimethylformamide. The peptide was further purified by partition chromatography on 'Sephadex' G-25 using the solvent system, n-butanol-acetic acid-water-pyridine (5:1:5:1 v/v), yield 30%, R$_f$A 0.49, paper electrophoresis at pH 2.1 and 6.5 showed a single spot, R$_f$ (relative to luliberin) 0.48 (pH 2.1), 0.23 (pH 6.5).

The starting materials used in the above procedure may be obtained as set out in the following Scheme 2.

Scheme 2

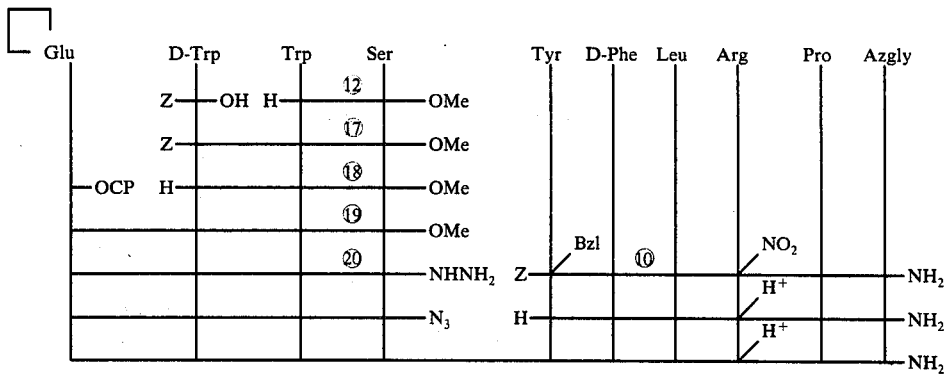

Step ⑰

As Step 13 Recrystallised from methanol. Yield 68%, m.p. 150°–151° C., R$_f$A 0.80, R$_f$B 0.78, R$_f$C 0.86, R$_f$D 0.74, R$_f$E 0.33, R$_f$F 0.69, R$_f$H 0.69, R$_f$Q 0.35.

Step ⑱

Catalytic reduction with 5% w/w palladium-on-charcoal in 80% v/v aqueous dimethylformamide for 5 hours at room temperature in presence of an equivalent of hydrogen chloride.

Step ⑲

As step 15 Yield 85%, m.p. 244°–246° C., R$_f$A 0.67, R$_f$B 0.74, R$_f$C 0.68, R$_f$D 0.65.

Step ⑳

As Step 16 Yield 86.1%, m.p. 234°–235° C.

EXAMPLE 3

Synthesis of L-pyroglutamyl-L-tryptophyl-L-seryl-L-tyrosyl-D-phenylalanyl-L-leucyl-L-arginyl-L-prolylazaglycine amide A solution of L-pyroglutamyl-L-tryptophyl-L-serine hydrazide (104 mg., 0.25 mmole) in dimethylformamide (2 ml.) was cooled to −20° C. and 5.9M HCl in dioxane (170 μl., 1.0 mmole) was added to it followed by t-butyl nitrite (30 μl., 0.275 mmole). After 20 minutes stirring the solution was neutralised with triethylamine (142 μl., 1.0 mmole). A precooled (−20° C.) mixture of L-tyrosyl-D-phenylalanyl-L-leucyl-L-arginyl-L-prolylazaglycine amide dihydrochloride (197 mg., 0.25 mmole, prepared as in Example 1) and triethylamine (36 μl., 0.25 mmole) in dimethylformamide (2 ml.) was added. The reaction mixture was stirred for 24 hours at 4° C. and was then applied directly to a 'Sephadex' LH-20 column. The column was eluted with dimethylformamide. The peptide was further purified by partition chromatography on 'Sephadex' G-25 using the solvent system, n-butanol-acetic acid-water (4:1:5 v/v), yield 32%, $R_fA$ 0.45, paper electrophoresis at pH 2.1 and 6.5 showed a single spot, $R_f$(relative to luliberin) 0.57 (pH 2.1), 0.66 (pH 6.5).

The starting materials used in the above procedure may be obtained as set out in the following Scheme 3.

Step 21

A solution of L-pyroglutamic acid 2,4,5-trichlorophenyl ester (3.4 g., 11 mmole), L-tryptophanyl-L-serine methyl ester hydrochloride (3.42 g., 10 mmole) and triethylamine (1.42 ml. 10 mmole) in dimethylformamide (30 ml.) was left for 48 hours at room temperature. Dimethylformamide was evaporated in vacuo and the residue was triturated with ethyl acetate-water, collected, washed with water, methanol-ether (5:1 v/v), ether and dried. Yield 1.82 g. (43.6%), m.p. 198° C., $R_fA$ 0.64, $R_fB$ 0.73, $R_fC$ 0.63, $R_fD$ 0.64, $R_fH$ 0.28, $R_fQ$ 0.11.

Step 22

A solution of L-pyroglutamyl-L-tryptophanyl-L-serine methyl ester (1.66 g, 4 mmole) in dimethylformamide (20 ml.) was treated with hydrazine hydrate (20 mmole) for 24 hours at room temperature. The solvent was removed in vacuo and the residue was crystallised from methanol to give the tripeptide hydrazide. Yield 1.09 g. (68%), m.p. 230°–231° C. (decomp.).

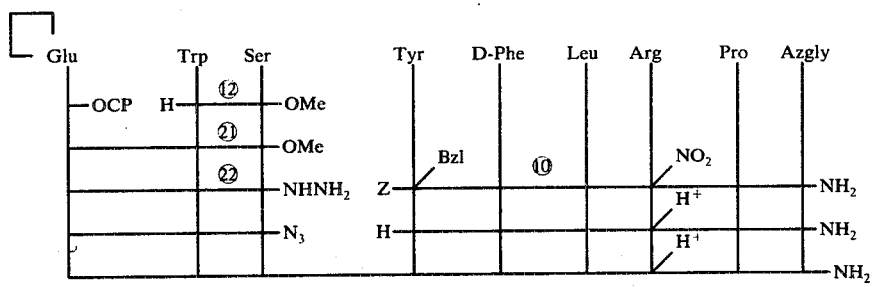

What we claim is:

1. A polypeptide of the formula:

Glu-D-Phe-Trp-Ser-Tyr-D-Phe-Leu-Arg-Pro-Azgly-NH$_2$     I and the pharmaceutically- and veterinarily-acceptable acid-addition salts thereof.

2. A pharmaceutical or veterinary composition comprising as active ingredient an effective amount of a polypeptide as claimed in claim 1 in association with a major amount of a non-toxic pharmaceutically- or veterinarily-acceptable diluent or carrier.

3. A method of controlling fertility in warm-blooded animals by inhibiting ovulation which comprises administering an effective amount of a polypeptide as claimed in claim 1.

Scheme 3